(12) United States Patent
Alba et al.

(10) Patent No.: US 10,176,889 B2
(45) Date of Patent: *Jan. 8, 2019

(54) SEGMENTING AND INTERPRETING A DOCUMENT, AND RELOCATING DOCUMENT FRAGMENTS TO CORRESPONDING SECTIONS

(71) Applicant: INTERNATIONAL BUSINESS MACHINES CORPORATION, Armonk, NY (US)

(72) Inventors: Alfredo Alba, Morgan Hill, CA (US); Anni R. Coden, Bronx, NY (US); Clemens Drews, San Jose, CA (US); Daniel F. Gruhl, San Jose, CA (US); Neal R. Lewis, San Jose, CA (US); Pablo N. Mendes, San Jose, CA (US); Cartic Ramakrishnan, San Jose, CA (US); Joseph F. Terdiman, San Rafael, CA (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/428,429

(22) Filed: Feb. 9, 2017

(65) Prior Publication Data
US 2018/0225258 A1    Aug. 9, 2018

(51) Int. Cl.
*H03M 5/00* (2006.01)
*H03M 7/00* (2006.01)
(Continued)

(52) U.S. Cl.
CPC ............. *G16H 10/60* (2018.01); *G06F 3/038* (2013.01); *G06F 17/2229* (2013.01);
(Continued)

(58) Field of Classification Search
CPC ......... G06F 17/24; G06F 19/322; G10L 15/26
(Continued)

(56) References Cited

U.S. PATENT DOCUMENTS 5,667,438 A    9/1997  Rehm
5,754,737 A    5/1998  Gipson
(Continued)

OTHER PUBLICATIONS

Nuance, "Medical Transcription Software & Speech Recognition Platform," "Features like automatic dictation file association, document routing, and integration deliver data to the EHR sooner—resulting in shortened billing cycles," Feb. 9, 2017. [Online] http://www.nuance.com/for-healthcare/medical-transcription-platforms/index.htm.

(Continued)

*Primary Examiner* — Cesar B Paula
*Assistant Examiner* — Luu-Phuong T Nguyen
(74) *Attorney, Agent, or Firm* — Conley Rose, P.C.

(57) ABSTRACT

A computer program product comprising a computer-readable storage medium having program instructions embodied therewith, the program instructions executable by a processor to cause the processor to receive a document having multiple section headers, segment the document into at least first and second sections based on the section headers, segment items in the first section into fragments and identify a section type for each of the fragments, determine that the identified section type for at least one of the fragments better matches a type of the second section than it matches a type of the first section, and re-locate the at least one of the fragments to the second section.

12 Claims, 8 Drawing Sheets

(51) Int. Cl.
*H03M 7/30* (2006.01)
*G16H 10/60* (2018.01)
*G06F 17/24* (2006.01)
*G10L 15/26* (2006.01)
*G06F 3/038* (2013.01)
*G06F 17/22* (2006.01)
*G06F 17/27* (2006.01)
*G06F 17/21* (2006.01)
*G06F 17/28* (2006.01)
*G06F 17/30* (2006.01)
*G06F 3/0482* (2013.01)

(52) U.S. Cl.
CPC .......... *G06F 17/24* (2013.01); *G06F 17/2745* (2013.01); *G10L 15/26* (2013.01); *G06F 3/0482* (2013.01); *G06F 17/211* (2013.01); *G06F 17/212* (2013.01); *G06F 17/27* (2013.01); *G06F 17/271* (2013.01); *G06F 17/274* (2013.01); *G06F 17/2705* (2013.01); *G06F 17/277* (2013.01); *G06F 17/2775* (2013.01); *G06F 17/2785* (2013.01); *G06F 17/28* (2013.01); *G06F 17/30684* (2013.01)

(58) Field of Classification Search
USPC ........................................................ 715/209
See application file for complete search history.

(56) References Cited

U.S. PATENT DOCUMENTS

| | | | |
|---|---|---|---|
| 5,799,268 A | 8/1998 | Boguraev | |
| 6,081,774 A * | 6/2000 | de Hita | G06F 17/30663 704/9 |
| 6,101,515 A | 8/2000 | Wical et al. | |
| 7,295,967 B2 | 11/2007 | Corman et al. | |
| 7,657,521 B2 | 2/2010 | Masarie | |
| 7,788,580 B1 * | 8/2010 | Goodwin | G06F 17/211 715/243 |
| 8,200,487 B2 * | 6/2012 | Peters | G06F 17/27 704/236 |
| 8,805,703 B2 | 8/2014 | Martin | |
| 8,949,254 B1 * | 2/2015 | De Datta | G06F 17/30011 707/751 |
| 9,152,763 B2 | 10/2015 | Carus | |
| 2003/0069908 A1 | 4/2003 | Anthony et al. | |
| 2004/0210573 A1 * | 10/2004 | Abe | G06F 17/30958 |
| 2004/0243545 A1 | 12/2004 | Boone | |
| 2004/0243936 A1 * | 12/2004 | Fukuda | G06F 17/30867 715/249 |
| 2005/0144184 A1 | 6/2005 | Carus | |
| 2005/0149861 A1 | 7/2005 | Bishop | |
| 2006/0074856 A1 * | 4/2006 | Liao | G06F 17/27 |
| 2007/0236742 A1 * | 10/2007 | Hale | G06F 17/2229 358/3.13 |
| 2008/0104032 A1 | 5/2008 | Sarkar | |
| 2008/0109739 A1 | 5/2008 | Khan | |
| 2009/0030671 A1 * | 1/2009 | Kwon | G06F 17/211 704/2 |
| 2009/0076792 A1 | 3/2009 | Lawson-Tancred | |
| 2009/0265187 A1 | 10/2009 | Boone | |
| 2010/0274584 A1 * | 10/2010 | Kim | G06F 19/322 705/3 |
| 2011/0313757 A1 * | 12/2011 | Hoover | G06F 17/274 704/9 |
| 2012/0130705 A1 | 5/2012 | Sun | |
| 2012/0173281 A1 | 7/2012 | DiLella | |
| 2012/0179961 A1 * | 7/2012 | Stollman | G06F 17/2785 715/243 |
| 2013/0185760 A1 | 7/2013 | Yamagishi | |
| 2013/0246098 A1 | 9/2013 | Habboush et al. | |
| 2014/0046696 A1 | 2/2014 | Higgins | |
| 2014/0067842 A1 * | 3/2014 | Chen | G06F 17/30386 707/758 |
| 2014/0172456 A1 | 6/2014 | Qian et al. | |
| 2014/0215306 A1 * | 7/2014 | Chiculita | G06F 17/248 715/234 |
| 2014/0365210 A1 | 12/2014 | Riskin | |
| 2015/0309989 A1 | 10/2015 | Brav et al. | |
| 2015/0356646 A1 | 12/2015 | Spitznagel | |
| 2016/0092428 A1 | 3/2016 | Ilic et al. | |
| 2016/0098480 A1 | 4/2016 | Nowson | |
| 2017/0004184 A1 | 1/2017 | Jain | |
| 2017/0249289 A1 * | 8/2017 | Simske | G06F 17/2264 |
| 2017/0286077 A1 | 10/2017 | Haswell et al. | |

OTHER PUBLICATIONS

Office Action dated Jan. 2, 2018, U.S. Appl. No. 15/428,480, filed Feb. 9, 2017, 43 pages.
Office Action dated Mar. 8, 2018, 19 pages, U.S. Appl. No. 15/627,173, filed Jun. 19, 2017.
Office Action dated Feb. 26, 2018, 23 pages, U.S. Appl. No. 15/627,169, filed Jun. 19, 2017.
Office Action dated Jun. 15, 2018, U.S. Appl. No. 15/428,480, filed Feb. 9, 2017, 47 pages.
Notice of Allowance dated Sep. 28, 2018, U.S. Appl. No. 15/627,173, filed Jun. 19, 2017.
Notice of Allowance date Sep. 19, 2018, U.S. Appl. No. 15/428,480, filed Jun. 19, 2017, 26 pages.
Notice of Allowance date Sep. 19, 2018, U.S. Appl. No. 15/627,169, filed Jun. 19, 2017, 26 pages.

* cited by examiner

SEGMENTING AND INTERPRETING A DOCUMENT, AND RELOCATING DOCUMENT FRAGMENTS TO CORRESPONDING SECTIONS

BACKGROUND

Documents are often composed in a disorganized manner. Varying types of information may be mixed together, information may be located in the wrong section of a document, or information may appear out of a desired sequence. For instance, a physician examining a patient may record the patient's family medical history in the same section of an electronic health record as the patient's personal medical history, despite the fact that family and personal medical histories are different types of information.

SUMMARY

In some embodiments, a computer program product comprises a computer-readable storage medium having program instructions embodied therewith, the program instructions executable by a processor to cause the processor to receive a document having multiple section headers, segment the document into at least first and second sections based on the section headers, segment items in the first section into fragments and identify a section type for each of the fragments, determine that the identified section type for at least one of the fragments better matches a type of the second section than it matches a type of the first section, and re-locate the at least one of the fragments to the second section.

In some embodiments, computer program product comprises a computer-readable storage medium having program instructions embodied therewith, the program instructions executable by a processor to cause the processor to segment items in a section of a document into multiple fragments, determine a section type of each of the multiple fragments, identify a pattern among the section types of the multiple fragments, and based on the pattern, re-locate at least one of the multiple fragments to another section in the document.

DETAILED DESCRIPTION

This disclosure describes various embodiments of systems and methods for segmenting, interpreting, and re-organizing written and oral documents. Written documents—for instance, an electronic health record or a travel agent's notes—and oral documents—for example, a doctor's self-dictated audio file—typically contain numerous fragments of information. Such fragments may include, for example and without limitation, words, terms, phrases, sentences, expressions, acronyms, abbreviations, symbols, and the like. These documents are often composed in a disorganized manner—due, for instance, to the author's personal time constraints, lack of adequate writing space, or disorganized thinking. This disclosure describes various embodiments of systems and methods for segmenting the fragments in such documents, interpreting the fragments to determine the type of information they contain, and re-arranging the fragments based on the interpretation in a well-organized manner. In this way, disorganized documents are re-synthesized as organized documents. Such re-organization techniques substantially improve the usefulness of documents that were previously too disorganized to be of any practical benefit. The techniques may be applied to vast numbers of stored, written documents (e.g., electronic records) and oral documents (e.g., audio files), thus increasing the availability of information on a mass scale. The techniques may similarly be applied dynamically (or "on-the-fly") to documents that are in the process of being composed so that fragments are placed in the proper sections of the document as they are provided by the user.

Figure 1:
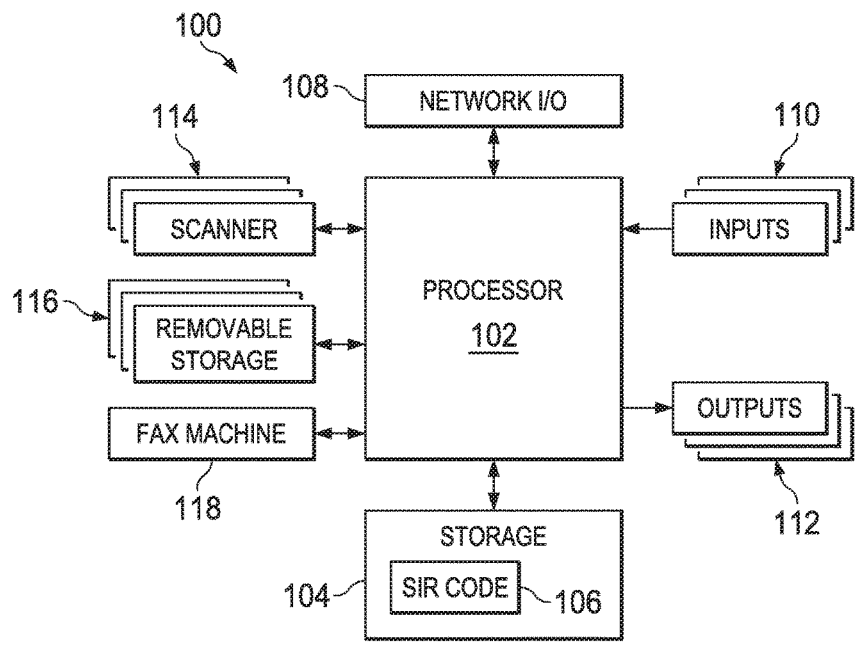
FIG. 1 is a block diagram of a system configured to implement some or all of the techniques disclosed herein.

FIG. 1 is a block diagram of a system 100 configured to implement some or all of the techniques disclosed herein. The system 100 includes a processor 102; storage 104 (e.g., random access memory (RAM), read-only memory (ROM)) storing segmentation, interpretation, and re-organization (SIR) code 106 (e.g., software, firmware) that may include one or more programs; a network input/output device 108 to facilitate communications with one or more remotely-located electronic devices; one or more inputs 110 (e.g., keyboard, mouse, touch screen, a microphone); one or more outputs 112 (e.g., a display, a printer); a scanner 114 to scan documents into electronic form; removable storage 116 (e.g., a thumb drive, a removable hard drive, a compact disc); and a fax machine 118. Other types of components that facilitate the performance of the various techniques described herein are contemplated and included within the scope of this disclosure. For example and without limitation, the system 100 may couple to or include a port for coupling the processor 102 to a mobile phone such that the processor 102 can download documents or other data from the mobile phone to the storage 104. Alternatively or in addition, the system 100 may be configured with Bluetooth capabilities (or other wireless protocols) to facilitate direct, wireless communication with one or more electronic devices.

In operation, the processor 102 executes the code 106, which causes the processor 102 to perform some or all of the actions described in this disclosure. Many of the actions described herein include operations on documents, including written documents (e.g., scanned, electronic copies of paper documents and electronic documents that were originally composed in electronic form) and oral documents (e.g., digital audio recordings). Accordingly, at least some of the components in the system 100 are suitable for receiving such documents and for providing the documents to the processor 102 for operation as described herein. For instance and without limitation, the network I/O 108 may couple to a private or public network, such as the Internet, and it may receive documents from other electronic systems. The network I/O 108 provides such received documents to the processor 102 for operation as described herein. The scanner 114 may scan paper documents and, after generating an electronic document by scanning the paper document, the scanner 114 may provide the electronic document to the processor 102 for operation. A removable storage 116 may store any number of electronic documents, including vast numbers of such documents (e.g., terabytes or more), that may be provided to the processor 102 for operation. Similarly, the local storage 104 may contain documents on which the processor 102 may operate as described herein. In some embodiments, the processor 102 may couple via the network I/O 108 to one or more other processors so that the processor 102 can delegate some or all of its document operation tasks to one or more of the other processors.

Executing the code 106 also causes the processor 102 to display a graphical user interface (GUI) on an output 112 (e.g., a display). The GUI may form part of an application with which a human user may interact to select documents, to view documents, to queue documents for analysis and re-organization, to review and adjust various settings associated with document analysis and re-organization, to compose documents orally or in written form or a combination thereof, etc. The user may use one or more input devices 110 to interact with the GUI displayed on the output 112 and to supervise the analysis and re-organization of documents. In at least some embodiments, the system 100 comprises a probabilistic machine, such as a cognitive computer that forms part of a neural network, that is capable of performing the various techniques described herein in a probabilistic manner. For example, when determining that a document fragment has been misplaced in a particular section of the document, the system 100 may perform a probabilistic analysis to determine the document section to which the fragment most likely belongs, and it may place the fragment in that section. Accordingly, the techniques described herein should be understood as having application in both deterministic and probabilistic computing machines.

Figure 2:
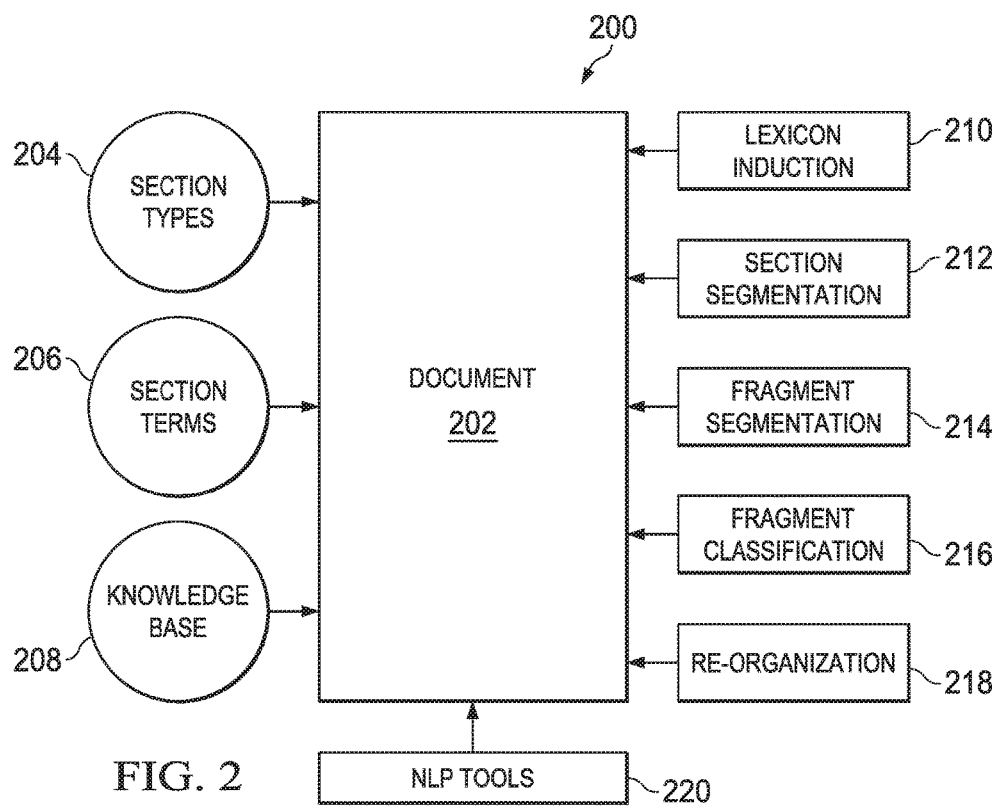
FIG. 2 is a conceptual diagram depicting various tools usable to segment, interpret, and re-organize a document.

FIG. 2 is a conceptual diagram 200 depicting a document 202 and various tools usable to segment, interpret, and re-organize the document 202. These tools may take any suitable form. For example, in some embodiments, one or more of these tools may take the form of executable code. In some embodiments, one or more of these tools may take the form of a database or other information classification or organization system. In some embodiments, one or more of these tools may take the form of hardware—for instance, neurosynaptic processor architectures as found in cognitive computers and neural networks. In some embodiments, one or more of these tools may combine any of the foregoing technologies. The tools depicted in the diagram 200 include section types 204; section terms 206; knowledge base 208; lexicon induction tool 210; section segmentation tool 212; fragment segmentation tool 214; fragment classification tool 216; re-organization tool 218; and natural language processing (NLP) tools 220.

The document 202 is the document on which the techniques described herein—for example, segmentation, interpretation, and re-organization are to be performed. The document may be written or oral and is any discrete set of information, such as a printed paper or collection of papers, an electronic paper or collection of papers (e.g., an electronic health record), and/or a digital audio file. The content of the document 202 may be divided into one or more sections, each with its own section header. For example, an electronic health record may include section headers directed to medication history, personal medical history, family health history, hospitalizations, and so on.

The section types 204 comprises a listing of section types that may be found in a particular type of document, such as the document 202. For instance, if the document 202 is an electronic health record, the section types 204 may include "family history," "medications," and the like. In some embodiments, the section types 204 comprises a listing of section types that may be found in a wide variety of documents, including, but not limited to, the document 202.

The section terms 206 comprises a listing of terms that may be used to refer to the section types 204. In at least some embodiments, the section terms 206 may include one or more synonyms that may be used to refer to one or more of the section types listed in section types 204. For example and without limitation, an entry in section types 204 entitled "prescription history" may correspond to entries in section terms 206 including "prescription history," "prescriptions," "Rx," "Rx history," "drug history," and the like. The section terms 206 may include individual words, phrases, terms, proper English usage, slang, and any other types of language that may be used to refer to one or more of the section types listed in section types 204.

The knowledge base 208 comprises numerous letters, words, phrases, sentences, symbols, spacing conventions, and other expressions that may be used in the content of each section of any type of document and may collectively and generically be referred to as "items." In some embodiments, the knowledge base 208 is large, possibly including tens of thousands or hundreds of thousands of items or more. In some embodiments, the knowledge base 208 is partitioned into two or more lexicons, with each lexicon containing items that correspond to one or more section types. In some embodiments, the knowledge base 208 is partitioned into two or more lexicons, with each lexicon containing items that correspond to one or more document types. For instance, the knowledge base 208 may contain a lexicon corresponding to electronic health records, and it may contain another lexicon corresponding to travel agent notes. In another example, the knowledge base 208 may be directed exclusively to electronic health records, and one of its lexicons may correspond to personal medical history while another one of its lexicons corresponds to prescription history. All such variations and permutations are contemplated and fall within the scope of this disclosure.

The lexicon induction tool 210 is an algorithm, encoded in executable code (e.g., code 106), that facilitates the modification of the lexicons in the knowledge base 208. In some embodiments, the lexicon induction tool 210 accepts new items manually input by a user via the aforementioned GUI, and the lexicon induction tool 210 stores the new items in the appropriate lexicon(s) of the knowledge base 208. In some embodiments, the human user may specify the appropriate lexicon(s) to which the new item(s) should be stored. In some embodiments, the lexicon induction tool 210 compares each new item to existing items in various lexicons, identifies the lexicon that has the items that best match the new item (e.g., using a thesaurus), and stores the new item to the best-matching lexicon. In some embodiments, the lexicon induction tool 210 automatically obtains new items from the document 202 that do not match any existing items in any of the lexicons. In such embodiments, the lexicon induction tool 210 compares the new items to existing items in the various lexicons, identifies the lexicon that has the items that best match the new items (e.g., using a thesaurus), and stores the new item to the best-matching lexicon. The scope of this disclosure is not limited to these techniques for expanding the content of the lexicons in the knowledge base 208.

The section segmentation tool 212 is an algorithm, encoded in executable code (e.g., code 106), that facilitates the segmentation of the document 202 into multiple, distinct sections. The steps of the algorithm are described in detail below with respect to FIGS. 3 and 4. In general, however, the section segmentation tool 212 uses the existing section headers (e.g., medical history, family history, smoking history, medications) in the document 202 to identify the boundaries of the sections and to segment the document into sections accordingly. To "segment" a document means to virtually or physically divide a document into multiple, distinct parts. A virtual division is one in which the processor 102 (FIG. 1) operates as if the document has been divided into multiple, distinct sections, even though the document has not actually been divided as such.

The fragment segmentation tool 214 is an algorithm, encoded in executable code (e.g., code 106), that facilitates the segmentation of items (e.g., words, phrases, sentences, symbols, numbers, and the like) in the document 202 into separate and distinct fragments. A fragment is an item or group of items in the document that is also found in one or more lexicons. For example, the word "pressure" is an item, but because it is unlikely to be found in a lexicon containing specialized terminology for, e.g., electronic health records, the word "pressure" would not qualify as a fragment. However, in the document 202 the word "pressure" may be found adjacent to the words "high blood," thus forming the phrase "high blood pressure." Because this phrase will be found in a lexicon for electronic health records, it qualifies as a fragment. Accordingly, the fragment segmentation tool 214 facilitates the review and comparison of items to various lexicons and, depending on the results of such comparisons, the segmentation of items into fragments. Segmentation may be virtual or physical, as explained above.

The fragment classification tool 216 is an algorithm, encoded in executable code (e.g., code 106), that facilitates the classification of fragments by the type of document section to which that fragment belongs. The fragment classification tool 216 may identify the section type to which the fragment belongs using any suitable technique—for instance, by matching one or more items appearing in the fragment to identical or similar (e.g., synonyms) items in one or more lexicons. If a fragment matches a particular lexicon, the fragment classification tool 216 determines that the fragment is of the section type corresponding to the matching lexicon. For example, the document 202 may be an electronic health record containing the fragment "patient exercises 20 min/day." The fragment classification tool 216 may interpret this fragment as belonging to a section relating to the patient's daily habits based on the fact that it expressly mentions the patient, the word "exercise," and a length of time per day, suggesting a daily activity. Accordingly, the fragment classification tool 216 classifies the fragment "patient exercises 20 min/day" as corresponding to the section type "patient daily habits." This fragment and section type, like all fragments, section types, and other examples provided herein, are merely illustrative and do not limit the scope of this disclosure.

The re-organization tool 218 is an algorithm, encoded in executable code (e.g., code 106), that facilitates the re-organization of the document 202. More particularly, the re-organization tool 218 facilitates the re-location of one or more fragments between different sections of the document 202. For instance, if classification of a particular fragment indicates that the fragment has been placed in the wrong section of the document 202, the re-organization tool 218 may excise that fragment from the wrong section and re-locate the fragment to a more appropriate section of the document 202. Alternatively or in addition, the re-organization tool 218 may generate a new section in the document 202 and may re-locate the misplaced fragment to the new section. Any number of fragments in a document may be re-located. In some embodiments, the re-organization tool 218 indiscriminately places the fragment into the proper section of the document 202. In some embodiments, the re-organization tool 218 is programmed to place the fragment in the proper section in a particular location or in a specific sequence relative to the other fragments in that section. For example, in the cognitive computing context, the computer may be trained or may automatically learn to place the fragment in certain areas of a section based on the content of other fragments already present in the section (e.g., in alphabetical order). The re-organization tool 218 also facilitates the proper placement of fragments into appropriate document sections dynamically—i.e., in real-time as the document is being composed.

FIG. 2 additionally depicts natural language processing (NLP) tools 220. At least some NLP tools are well-known in the art and thus their implementations are not described in detail here. The NLP tools 220 may include, without limitation: automatic summarization NLP tools; coreference resolution NLP tools; discourse analysis NLP tools; machine translation NLP tools; morphological segmentation NLP tools; named entity recognition NLP tools; natural language generation NLP tools; natural language understanding NLP tools; optical character recognition (OCR) NLP tools; part-of-speech tagging NLP tools; parsing NLP tools; relationship extraction NLP tools; sentence breaking/sentence boundary disambiguation NLP tools; speech recognition NLP tools; speech segmentation NLP tools; topic segmentation and recognition NLP tools; word segmentation NLP tools; word sense disambiguation NLP tools; information retrieval NLP tools; information extraction NLP tools; speech processing NLP tools; text-proofing NLP tools; and text-to-speech NLP tools. The scope of disclosure is not limited to these NLP tools. The processor 102 may use one or more of these NLP tools as may be appropriate—e.g., to accomplish any of the techniques described herein.

Figure 3:
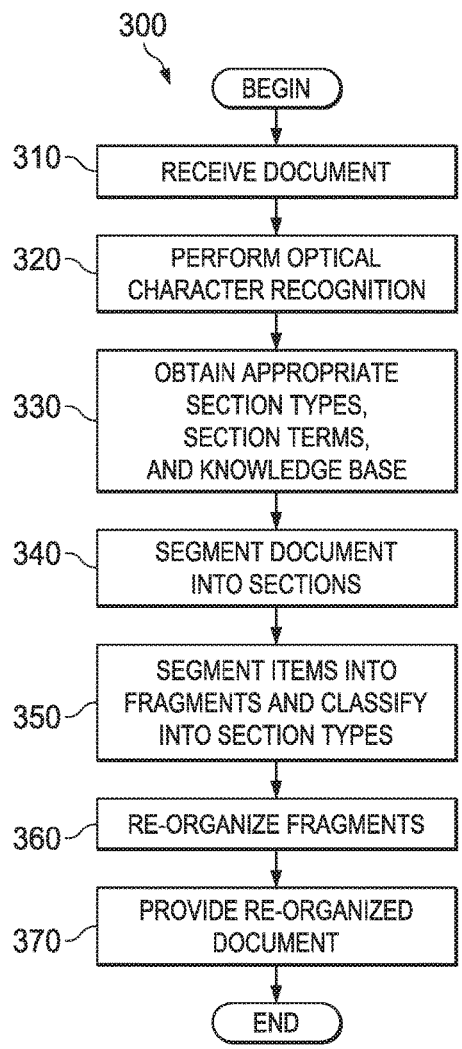
FIG. 3 is a flow diagram of an illustrative document segmentation, interpretation, and re-organization operation.

FIG. 3 is a flow diagram of an illustrative document segmentation, interpretation, and re-organization process 300. The process 300 begins with receiving a document (step 310), such as the document 202 of FIG. 2, and performing optical character recognition (OCR) on the document (step 320)—for instance, in the case of a written document having images of text that is converted into a document having machine-encoded text. In the case of oral documents, such as digital audio files, OCR may be omitted, but another suitable NLP tool—such as a speech recognition NLP tool—may be used to determine the content of the oral document and to convert the oral document to a text-based written document for subsequent processing. Such subsequent processing is the same or similar as the processing of written documents that were not previously in oral form.

The process 300 next comprises obtaining the section types, section terms, and knowledge base appropriate to the received document (step 330), such as the section types 204, section terms 206, and knowledge base 208 of FIG. 2. For example and without limitation, in the case of an electronic health record, the step 330 comprises obtaining the section types and section terms relating to, e.g., personal medical history, family health history, medications, social habits, smoking habits, etc. An appropriate knowledge base for the electronic health record may include a plurality of lexicons for the various section types and section terms obtained. The section types, section terms, and knowledge bases may be stored in a suitable local repository, such as in the removable storage device 116, or in a remotely-located storage system that is accessible via the network I/O 108 (FIG. 1). When obtained in step 330, the section types, section terms, and knowledge bases may be stored in, e.g., the local storage 104.

Figure 4:
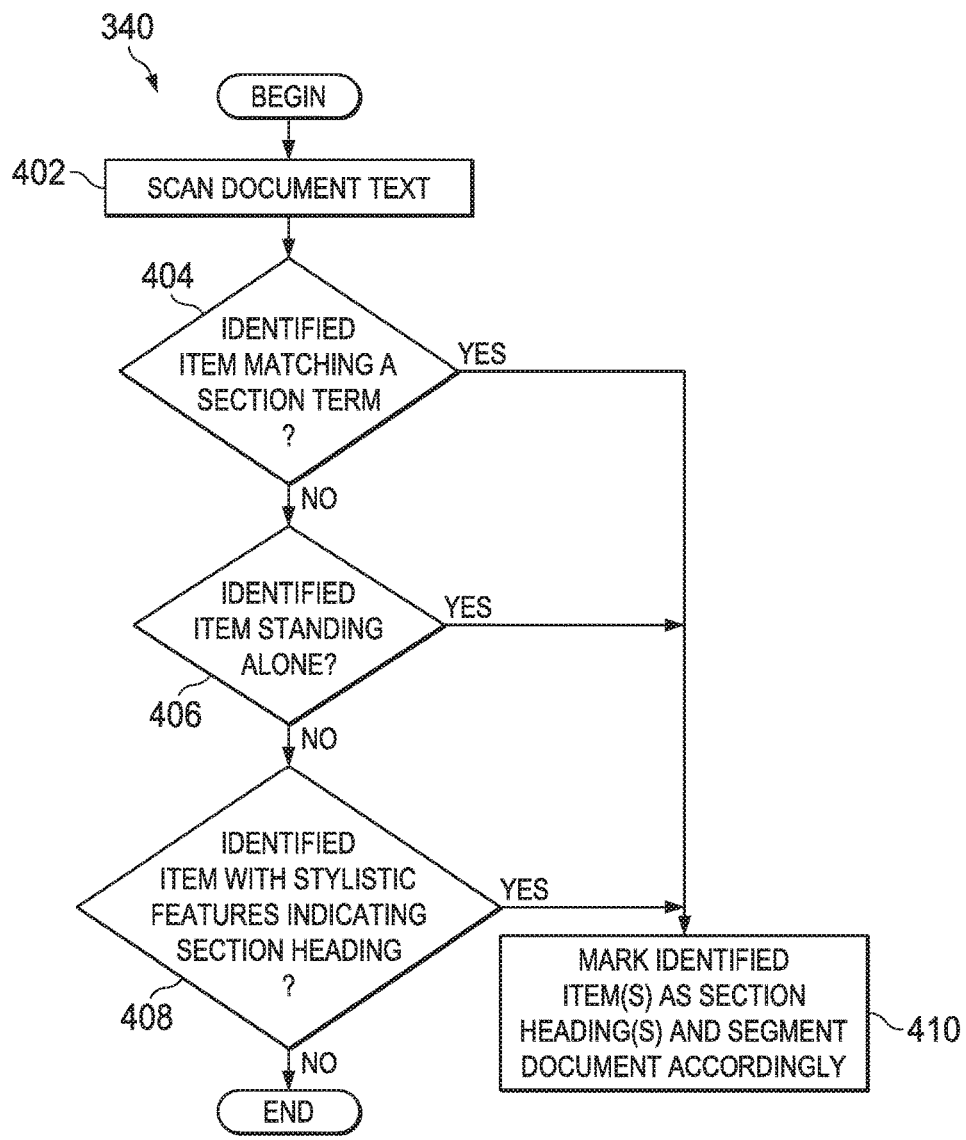
FIG. 4 is a flow diagram of an illustrative document section identification and segmentation operation.

The process 300 subsequently comprises segmenting the document into sections (step 340). The processor 102 may use any of a variety of tools to perform such segmentation, including, without limitation, the section segmentation tool 212 and one or more of the NLP tools 220. FIG. 4 is a flow diagram of an illustrative document section identification and segmentation process 340, which describes the step 340 of FIG. 3 in more detail. The process 340 begins by scanning the document text (step 402). As the document is already in machine-readable form (e.g., due to the aforementioned OCR operation for written documents or the speech recognition operation for oral documents), step 402 entails the processor 102 examining the text of the document to identify the individual items (e.g., letters, words, spaces, phrases, sentences, symbols) contained in the document. The process 340 further comprises determining whether one or more items matching one or more section terms have been identified (step 404). For example, in the context of an electronic health record and section terms 206 containing terms suitable for electronic health records, step 404 may entail the processor 102 identifying the terms "prescription medications" and "personal medical history" in the document. If such section terms are identified in the document, the process 340 comprises marking the identified text as section heading(s) and segmenting the document accordingly (step 410). As previously explained, document segmentation may be virtual or physical. Section segmentation, as in step 410, entails the processor 102 identifying a first section heading, identifying the items below the first section heading, identifying a second section heading (or the end of the document), and segmenting between the second section heading and the end of the items under the first section heading.

If no section terms are found in step 404, the process 340 comprises identifying items that stand alone—e.g., items with one or more spaces above and below the items, as is typical of section headings in many documents (step 406). If one or more such items are identified, the process 340 comprises marking the identified items as section heading(s) and segmenting the document accordingly (step 410). Otherwise, if stand-alone items are not identified in step 406, the process 340 includes identifying items with stylistic features indicating section headings (step 408). For example and without limitation, such stylistic features may include bolding, underlining, italics, and the like. If one or more such items are identified, the process 340 comprises marking the identified items as section heading(s) and segmenting the document accordingly (step 410). In some embodiments, two or more of the foregoing tests may be combined to reduce the incidence of false positives. In addition to or in lieu of one or more of the tests in steps 404, 406, and 408, one or more other tests may be used to identify section headings. The tests described in steps 404, 406, and 408 are illustrative and do not limit the scope of the disclosure.

Figure 5:
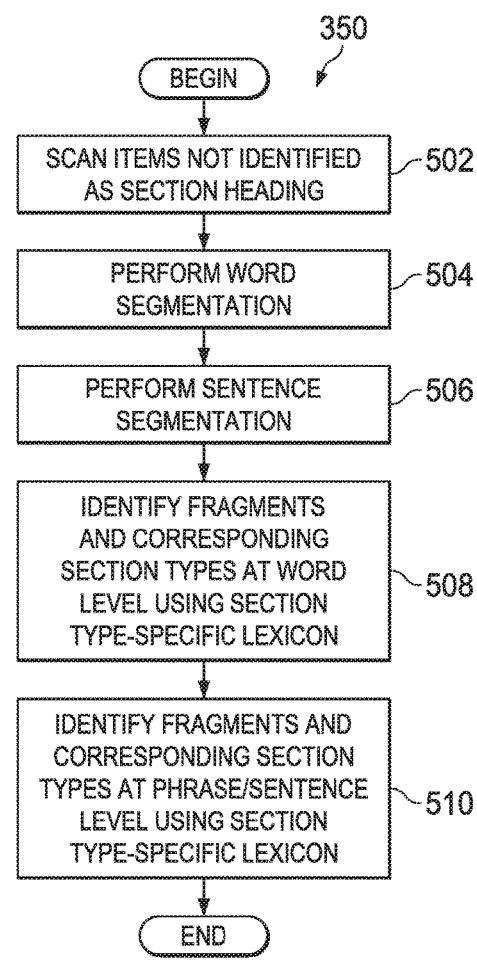
FIG. 5 is a flow diagram of an illustrative document segmentation and interpretation operation.

Referring again to FIG. 3, after the document has been segmented by section (step 340), the process 300 comprises segmenting the items into fragments and classifying the fragments by section type (step 350). In at least some embodiments, the processor 102 uses the fragment segmentation tool 214 and the fragment classification tool 216 (FIG. 2) to perform this step. The step 350 is described in greater detail by the process 350 depicted in FIG. 5. The process 350 begins by scanning the items not identified as section headings in the process 340 (step 502). The process 350 continues by performing word segmentation (step 504). Word segmentation entails the processor 102 segmenting the various items in each section of the document on an individual word basis. The processor 102 may accomplish this, for example, by identifying single spaces between text, which likely indicates separation between words. Other techniques also may be used. Similarly, the process 350 entails performing sentence segmentation (step 506), which entails the processor 102 segmenting the various items in each section of the document on an individual sentence basis. The processor 102 may accomplish this, for instance, by identifying punctuation marks (e.g., periods, exclamation marks, question marks) between text, which likely indicates separation between sentences. Alternatively or in addition, the processor 102 may identify double spaces, as double spacing is commonplace in between two separate sentences. As a result of performing steps 504 and 506, the processor 102 has identified each word and each sentence in the document. The scope of disclosure is not limited to segmenting on a word basis and a sentence basis. Other items may be used as a basis for segmenting—for example, segmenting on a paragraph basis.

The process 350 subsequently includes identifying fragments and corresponding section types at the word level using a section-type specific lexicon (step 508). Stated another way, the step 508 comprises the processor 102 using a lexicon appropriate for the type of section being examined to identify fragments in the section at the word level and the section types corresponding to those fragments. For instance, in step 508 the processor 102 may use an "exercise habits" lexicon to identify fragments in the "exercise habits" section of a document. In this instance, the processor 102 identifies individual words that find matching entries in the lexicon. These words with matching entries are fragments, and the processor 102 classifies these fragments as corresponding to the section type "exercise habits."

After completing step 508, there may be at least some words remaining in the "exercise habits" section that did not correspond to any matching entries in the "exercise habits" lexicon. In such cases, it is possible or likely that the words themselves have no meaning with respect to the "exercise habits" lexicon, but when taken in tandem with other, surrounding words, phrases and/or sentences are formed that have matching entries in the "exercise habits" lexicon. Accordingly, in step 510, the processor 102 identifies fragments and corresponding section types at the phrase and/or sentence level using a section type-specific lexicon (step 510). In any step that entails the identification of a fragment section type, a single fragment may correspond to one section type or to multiple, differing section types. The process 350 is then complete. The steps of the process 350 shown in FIG. 5 and described above are merely illustrative. They do not limit the scope of this disclosure. As with the steps in any method described herein, the steps in the process 350 may be added, deleted, rearranged, or modified as desired and as appropriate. Other techniques for segmenting items in the various document sections into fragments and classifying the fragments by section type (i.e., "interpreting" the fragments) are contemplated and included within the scope of this disclosure.

Figure 6:
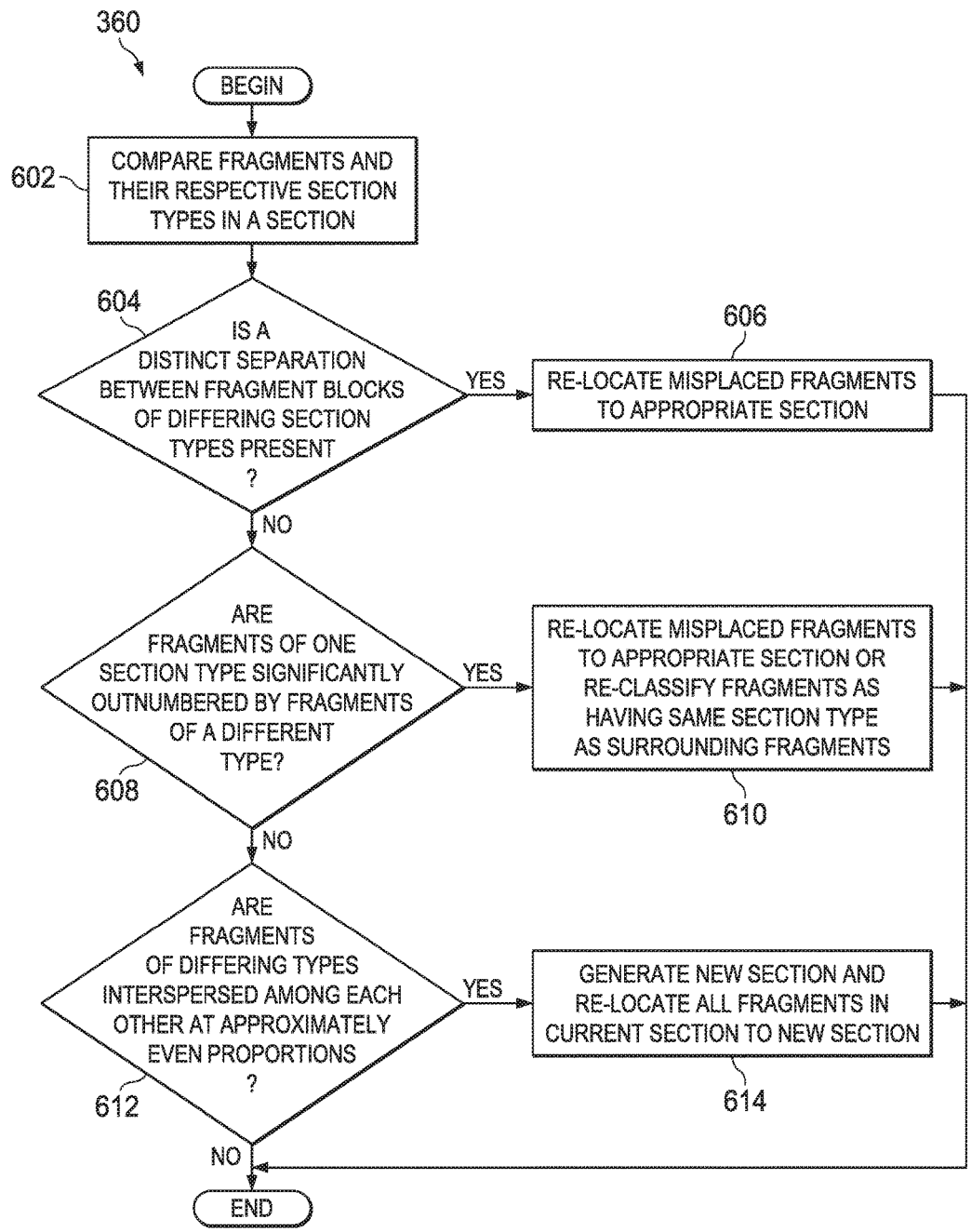
FIG. 6 is a flow diagram of an illustrative document re-organization operation.

Referring again to FIG. 3, after completion of the step 350, the process 300 comprises re-organizing the fragments of the document according to their identified section types (step 360). The processor 102 may perform this step using the re-organization tool 218. FIG. 6 is a flow diagram of an illustrative document re-organization process 360. The process 360 facilitates the identification of one or more patterns of fragments in a section to determine whether and which fragments should be re-located to other sections. The process 360 begins by comparing document fragments and their respective section types within a section (step 602). For example, in an electronic health record section entitled "medication history," there may be several fragments, each relating to a different medication. As a result of performing the step 350, these fragments would all be classified as "medication history" fragments. In addition, the "medication history" section may include a fragment relating to the patient's exercise habits. As a result of performing the step 350, this fragment would be classified as an "exercise habits" fragment. Accordingly, when performing the step 602, the processor 102 would compare the section types of these fragments and determine that all but one of the fragments corresponds to the "medication history" section type. The processor 102 would further determine that the fragment that is not of the "medication history" section type is of the "exercise habits" section type.

Next, in step 604, the processor 102 determines based on the comparison of step 602 whether the section being analyzed contains a distinct separation between large fragment blocks of different section types. For example, a "medication history" section may contain fragments, 51% of which are classified as having a "medication history" section type and 49% of which are classified as having an "exercise habits" section type. Further, the 51% of fragments that correspond to the "medication history" section type may form a contiguous block, and the 49% of fragments that correspond to the "exercise habits" section type also may form a contiguous block, with the two blocks abutting each other. This indicates a clear separation between the two types of fragments. The precise requirement for fragments in a section to have a "distinct separation" as described in step 604 depends on, e.g., a programmer programming the code 106 and/or any of the NLP tools described above. When the condition described in step 604 is met, the process 360 comprises re-locating the misplaced fragments to the appropriate section (step 606)—e.g., relocating the 49% of fragments classified as "exercise habits" to the "exercise habits" section of the document.

If the requirement of step 604 is unmet, the process 360 comprises determining whether the fragments of one section type in the section being analyzed are significantly outnumbered by fragments of a different type (step 608). For instance, a "medication history" section of the document may include numerous fragments, 95% of which are identified in step 350 of process 300 (FIG. 3) as being "medication history" fragments, and the remaining 5% of which are identified as being "exercise habits" fragments. The threshold at which a first type of fragment is "significantly outnumbered" by another type of fragment may be programmed as desired. If a type of fragment is significantly outnumbered based on the analysis in step 608, the process 360 includes re-locating the misplaced fragment(s) to the appropriate section(s) (step 610). Alternatively, the process 360 may include re-classifying the outnumbered fragments so that they have the same section type as the section in which they are presently located (step 610), and the appropriate lexicon(s) may be updated accordingly to reflect this re-classification.

If the requirement of step 608 is unmet, the process 360 comprises determining whether the fragments of differing types are interspersed among each other in approximately even proportions (step 612). For instance, fragments of two different types may be arranged in a section in an alternating fashion. This pattern may suggest that neither of the two types of fragments belongs in the section in which they are found, and it may also suggest that they belong together, meaning that they do not belong in any of the currently available sections. Accordingly, the process 360 comprises generating a new section and re-locating all fragments in the section being analyzed to the new section (step 614). The process 360 is then complete. If, during performance of the process 360, a fragment is determined to correspond to multiple sections of differing section types, that fragment may be copied and placed within one or more of the corresponding, multiple sections.

Referring again to FIG. 3, after the step 360 is complete, the process 300 comprises providing the re-organized document to, e.g., a display, storage, or a device communicably coupled to the processor 102 (step 370). In the case of a document that was converted from an oral document prior to analysis and re-organization, the step 370 comprises converting the document back to an oral document in audio form (e.g., using text-to-speech NLP tools). The oral document may then be provided to, e.g., a speaker, storage, or a device communicably coupled to the processor 102 (step 370).

Figure 7A:
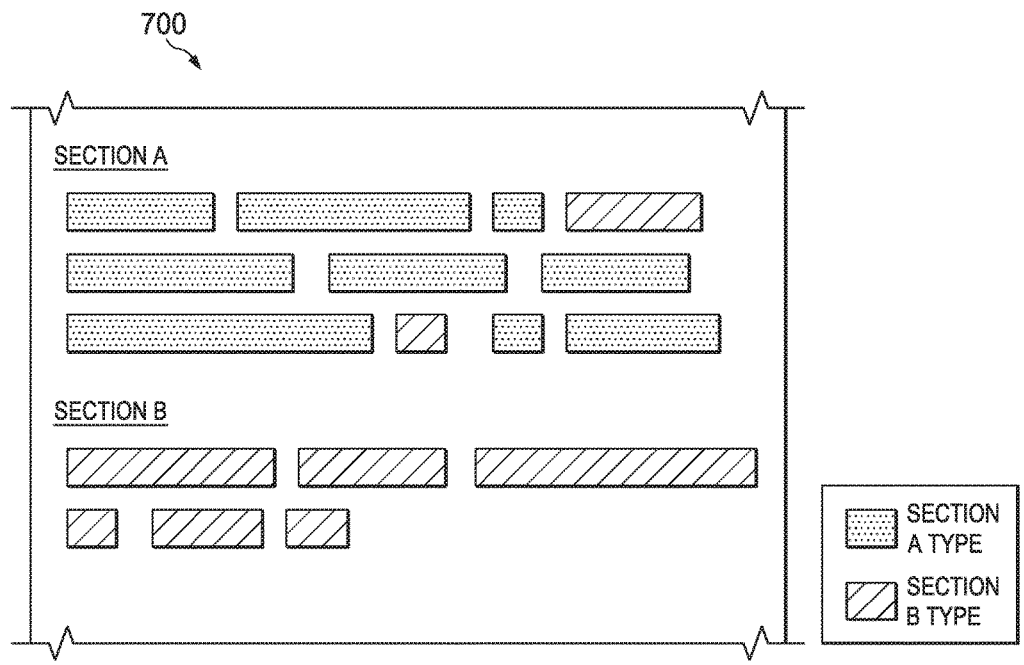
FIGS. 7A-7B are conceptual illustrations of an oral or written document segmentation, interpretation, and re-organization operation.
Figure 7B:
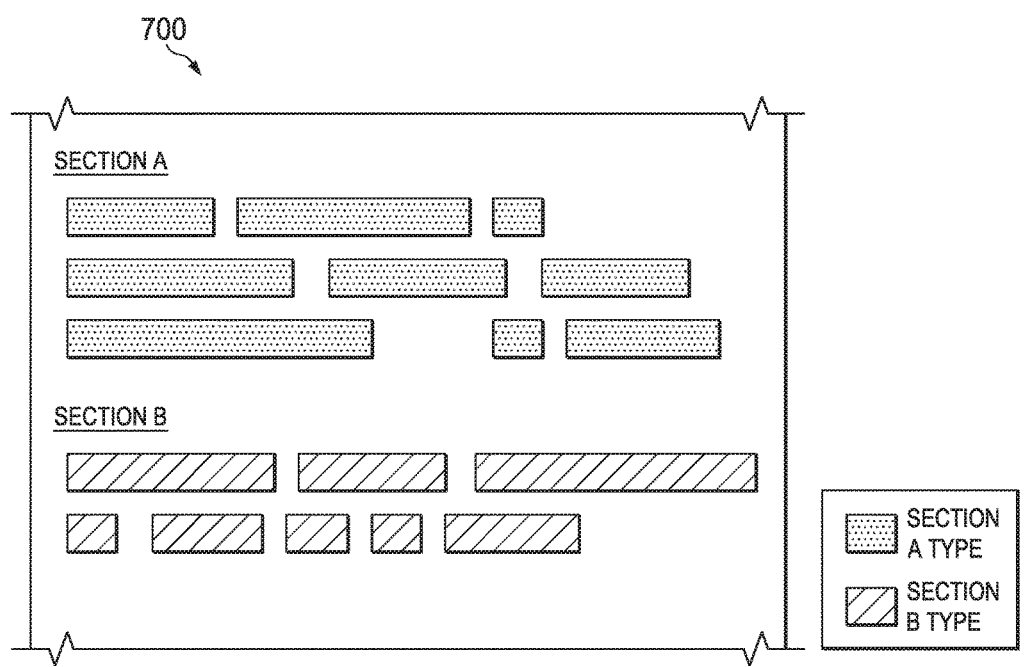

FIGS. 7A-7B are conceptual illustrations of a document segmentation, interpretation, and re-organization operation. FIG. 7A shows a portion 700 of a document. The portion 700 includes sections A and B. Section A contains 11 fragments, and section B contains six fragments. The fragments in section A have been identified as corresponding to two different section types. As the legend in FIG. 7A indicates, the majority of fragments in section A have been identified as corresponding to the "section A" type, while two of the fragments in section A have been identified as corresponding to the "section B" type. All of the fragments in section B have been identified as corresponding to the "section B" type. Because none of the fragments in section B are misplaced, none of those fragments require re-location. However, two of the fragments in section A are misplaced. Because these two fragments are significantly outnumbered by the other fragments (as described in step 608 of FIG. 6), the processor 102 may determine that these two fragments are misplaced and may re-locate them to section B, as FIG. 7B indicates.

Figure 8A:
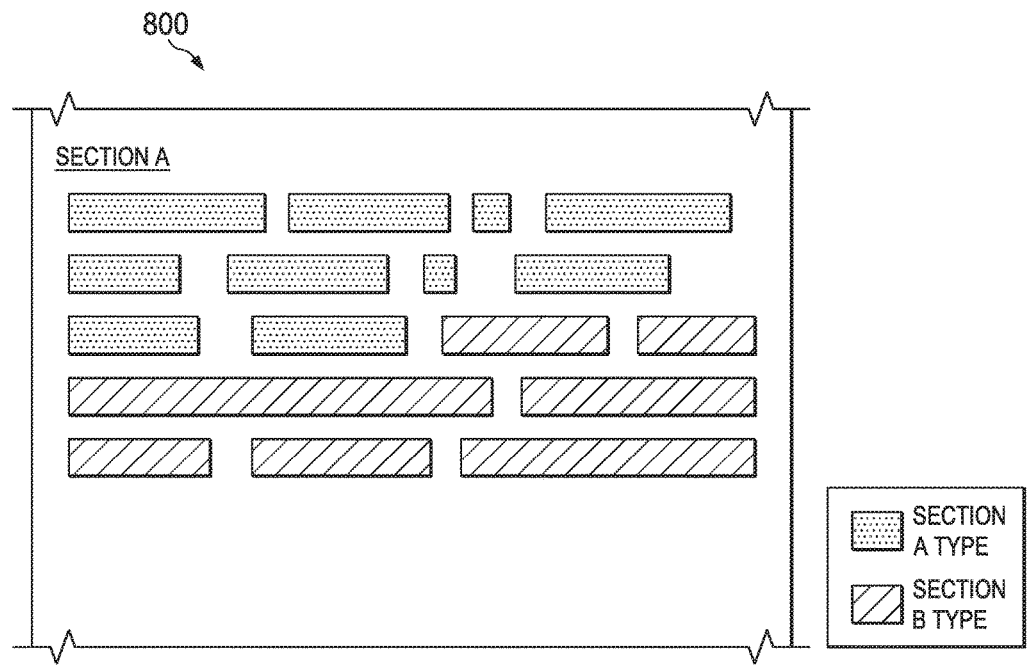
FIGS. 8A-8B are conceptual illustrations of an oral or written document segmentation, interpretation, and re-organization operation.
Figure 8B:
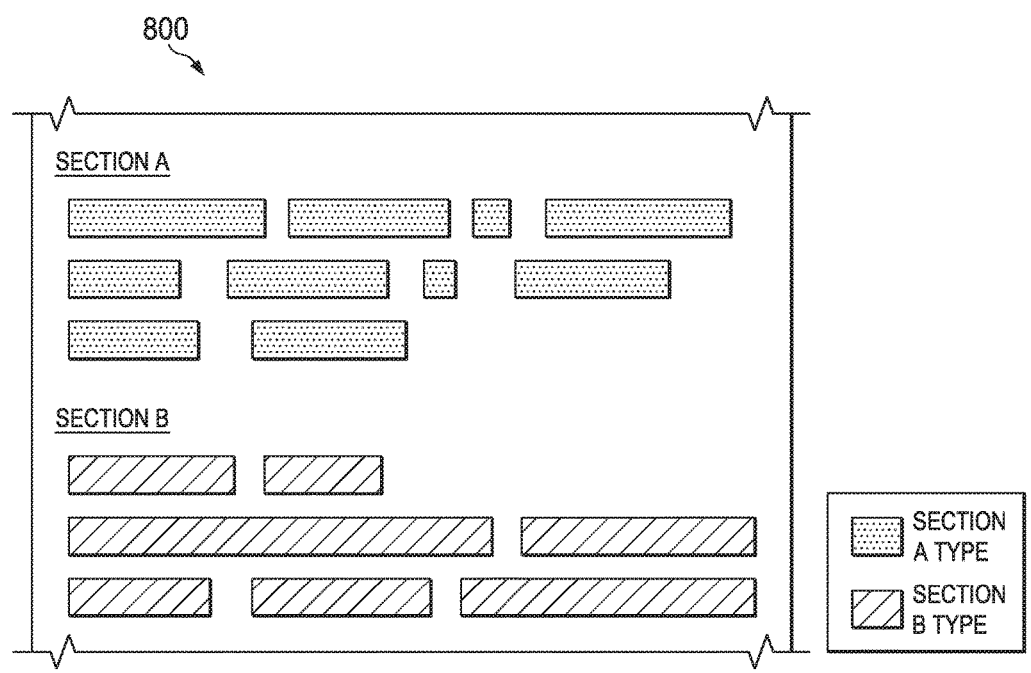

FIGS. 8A-8B are conceptual illustrations of another document segmentation, interpretation, and re-organization operation. FIG. 8A shows a portion 800 of a document. The portion 800 includes section A. Section A contains 17 fragments, some of which are identified as corresponding to the "section A" type, and some of which are identified as corresponding to the "section B" type. The section A type of fragments form a contiguous block, as do the section B type fragments. There is a distinct separation between the fragment blocks. This distinct separation between fragment blocks suggests that the block containing section B type fragments are misplaced in section A and should be re-located to section B (as described in steps 604 and 606). FIG. 8B shows this re-location.

Figure 9A:
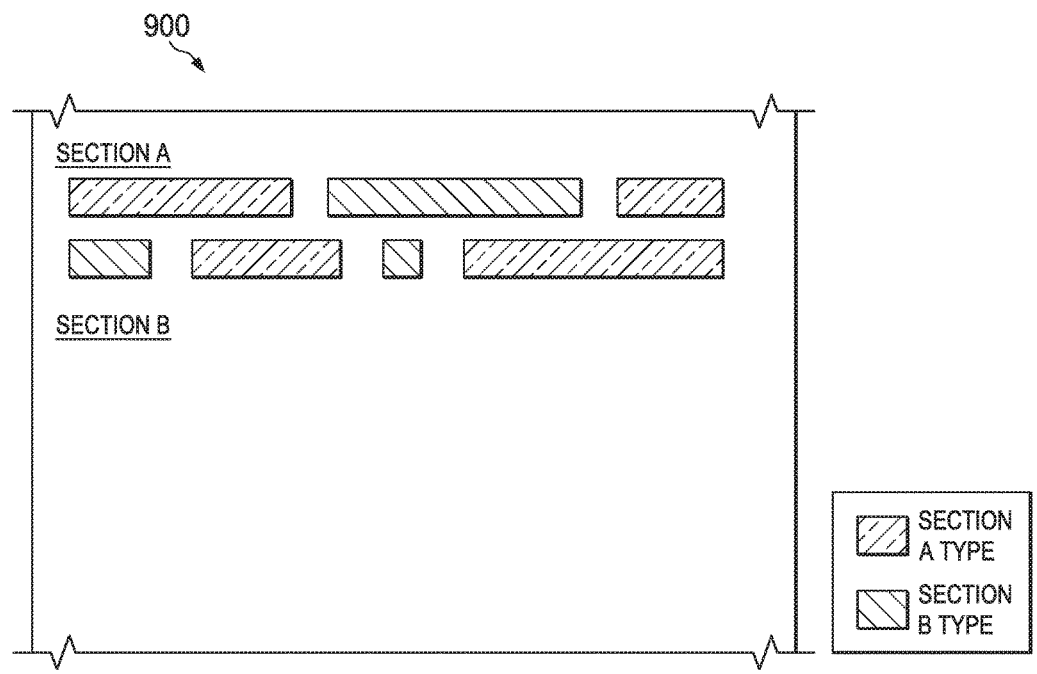
FIGS. 9A-9B are conceptual illustrations of an oral or written document segmentation, interpretation, and re-organization operation.
Figure 9B:
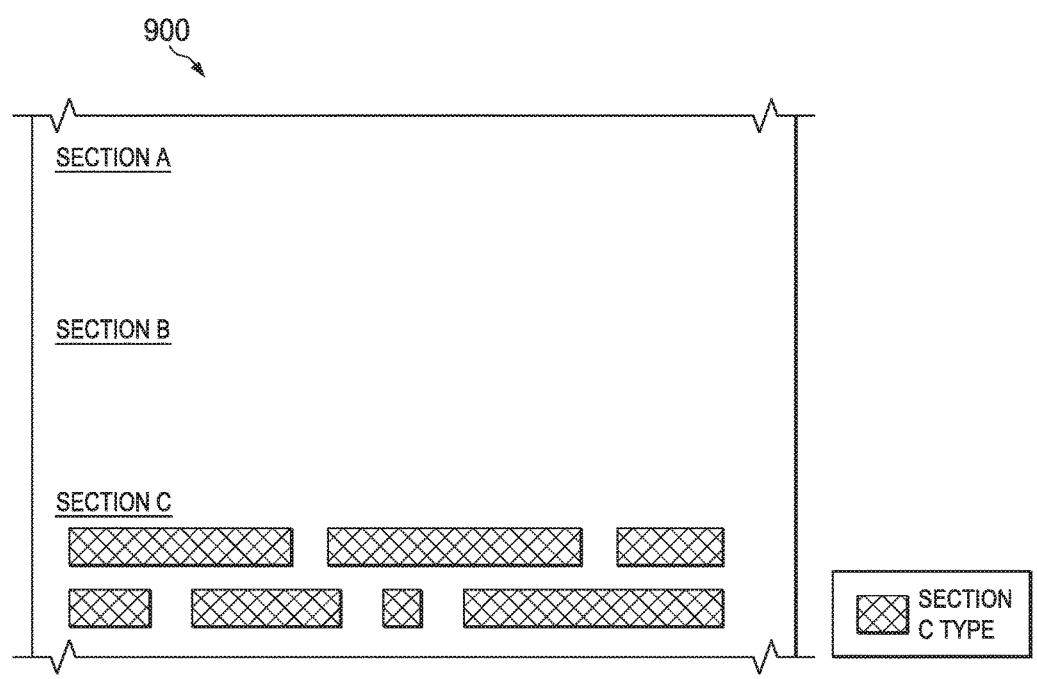

FIGS. 9A-9B are conceptual illustrations of another document segmentation, interpretation, and re-organization operation. FIG. 9A depicts a portion 900 of a document. The portion 900 includes section A, which contains fragments of section types A and B. As shown, the fragments are interspersed roughly equally among each other such that they appear to be in an alternating pattern. The specific distribution of fragments required to qualify as being in an alternating pattern may be programmed as desired by the programmer of the code 106. Because of this alternating pattern, the processor 102 determines that the fragments in section A do not belong in section A or in section B (as described in step 612 of FIG. 6). Because of their alternating pattern, the fragments appear to belong together, and so they may be deemed to have been misclassified and are re-classified as belonging to a new section C. Accordingly, the processor 102 generates a new section C, re-classifies the fragments as corresponding to the section C type, and re-locates the fragments to the new section C. FIG. 9B shows this re-location.

Figure 10:
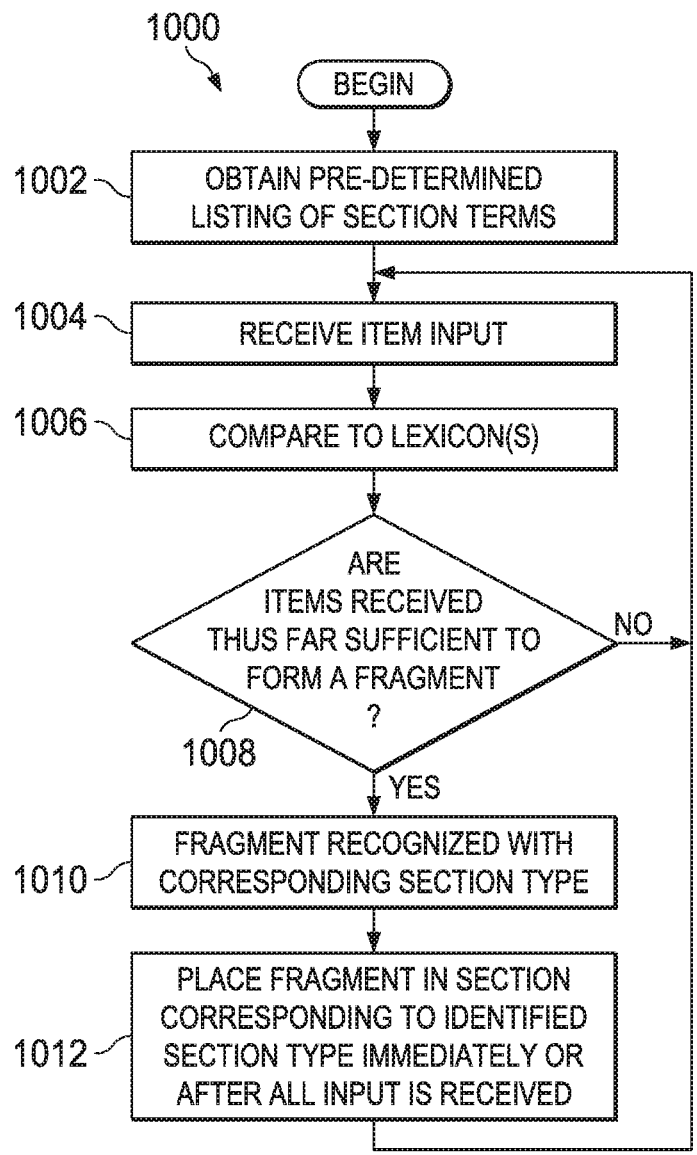
FIG. 10 is a flow diagram of a process 1000 used to organize documents during composition.

At least some of the foregoing techniques may find application with documents that have already been fully composed. In some embodiments, at least some of the foregoing techniques may be applied to documents that are in the process of being composed so that the documents are organized dynamically, or "on-the-fly." FIG. 10 is a flow diagram of a process 1000 used to organize documents during composition. As with other processes disclosed herein, the processor 102 illustrates computer systems that may implement the process 1000. The process 1000 begins by obtaining a predetermined listing of the section terms that will be used in composing the document (step 1002). These section terms—like section terms 206 in FIG. 2—are used as section headers and are used to classify the items collected during the process 1000.

The process 1000 next comprises receiving an input item (step 1004). The item may be received via an input device 110 (FIG. 1), via the network I/O 108, or via any other suitable device. As explained above, items may be characters, words, phrases, sentences, symbols, spaces, numbers, and the like, although the scope of disclosure is not limited to this illustrative listing. The process 1000 next includes comparing the received item to multiple lexicons (e.g., in the knowledge base 208 in FIG. 2) to find matches (step 1006). If the item matches an entry in a lexicon, then the item may be sufficient to form a fragment (step 1008). If the item matches more than one entry in a lexicon, or if the item matches one or more entries in multiple lexicons, the item may be sufficient to form a fragment (step 1008). However, if the item fails to find a match in any lexicon, the item likely is not sufficiently specific to form a fragment (step 1008), and the item must be combined with one or more subsequently-received items to increase the chances of finding a match in one or more lexicons. For example, the item "patient's" likely is not sufficiently specific to find a match in any lexicon, but when taken in tandem with the subsequently-received item "blood pressure," the fragment "patient's blood pressure" will likely find a match in the lexicon of the "vital signs" section type.

Thus, if the items received thus far are insufficient to form a fragment (step 1008), control of the process flow returns to step 1004. However, if the item(s) received are sufficient to form a fragment (step 1008), the process 1000 comprises recognizing the fragment with the corresponding section type (step 1010), and the process 1000 further comprises placing the fragment in the section corresponding to the identified section type either immediately or after all input for the document has been received (step 1012). Control of the process 1000 then returns to step 1004.

In some embodiments, dynamic document organization of the type described in process 1000 is performed so that organizational changes are reflected in the document in real time as the document is being composed. In some embodiments, dynamic document organization of the type described in process 1000 is performed so that organizational changes are stored (e.g., in the storage 104 of FIG. 1) until document composition is complete, at which time the organizational changes are rendered in the document. During both dynamic document organizational processes and other organizational types of processes, the processor 102 may prompt a user at various times and for various reasons—for example, to obtain permission to move a particular fragment from one section to another; to move a particular fragment to a particular section when the document is being organized dynamically (i.e., "on-the-fly"); to determine to which of multiple sections a fragment best belongs; to make on-the-fly edits to fragments to facilitate more accurate classification of fragment section type, and so on. The processor 102 may present such prompts to the user using, e.g., one or more outputs 112, and the processor 102 may receive responses to such prompts from the user via, e.g., one or more inputs 110. Finally, one or more of the systems and methods described with respect to FIGS. 1-9B may find application in conjunction with dynamic document organization techniques, such as that described with respect to FIG. 10.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/ or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

What is claimed is:

1. A computer program product comprising a non-transitory computer-readable storage medium having program instructions embodied therewith, the program instructions executable by a processor to cause the processor to:

receive a document having section headers;

segment the document into at least first and second sections based on the section headers;

segment items in the first section into fragments including a first fragment and a second fragment;

identify a section type for each of the fragments using multiple section type-specific lexicons that include a first section type-specific lexicon that corresponds to a section type of the first section and a second section type-specific lexicon that corresponds to a section type of the second section, wherein the first fragment is identified as corresponding to a different section type than the second fragment;

determine a first quantity of first fragments of the multiple fragments and a second quantity of second fragments of the multiple fragments, wherein the first fragments correspond to a first section type of the first section and the second fragments correspond to a second section type of a second section of the document;

determine that the first quantity of the first fragments exceeds the second quantity of the second fragments by a predetermined quantity; and based on exceeding the predetermined quantity, re-locate the second fragments to the second section in the document or reclassify the second fragments to correspond to the first section type.

2. The computer program product of claim 1, wherein the document comprises an electronic health record.

3. The computer program product of claim 1, wherein the items include non-alphabetical and non-numerical symbols.

4. The computer program product of claim 1, wherein, to segment the items into fragments, the program instructions are executable by the processor to cause the processor to identify a portion of the items that match one of the multiple section type-specific lexicons.

5. The computer program product of claim 1, wherein, to segment the items into fragments, the program instructions are executable by the processor to identify individual words in the first section that correspond to one of the multiple section type-specific lexicons.

6. The computer program product of claim 1, wherein, to segment the items into fragments, the program instructions are executable by the processor to identify phrases and sentences in the first section that correspond to one of the multiple section type-specific lexicons.

7. A computer program product comprising a non-transitory computer-readable storage medium having program instructions embodied therewith, the program instructions executable by a processor to cause the processor to:
segment items in a first section of a document into multiple fragments; determine a section type of each of the multiple fragments;
determine a first quantity of first fragments of the multiple fragments and a second quantity of second fragments of the multiple fragments, wherein the first fragments correspond to a first section type of the first section and the second fragments correspond to a second section type of a second section of the document;
determine that the first quantity of the first fragments exceeds the second quantity of the second fragments by a predetermined quantity; and
based on exceeding the predetermined quantity, re-locate the second fragments to the second section in the document or reclassify the second fragments to correspond to the first section type.

8. The computer program product of claim 7, wherein the program instructions executable by the processor cause the processor to reclassify the second fragments to correspond to the first section type when the first quantity of the first fragments exceeds the second quantity of the second fragments by the predetermined quantity, and wherein the program instructions are further executable by the processor to cause the processor to update a section type-specific lexicon corresponding to the first section type to reflect the reclassification.

9. The computer program product of claim 7, wherein the program instructions are executable to cause the processor to generate the second section based on exceeding the predetermined quantity.

10. The computer program product of claim 7, wherein the document comprises a written representation of an oral document.

11. A computer program product comprising a non-transitory computer-readable storage medium having program instructions embodied therewith, the program instructions executable by a processor to cause the processor to:
segment the document into multiple sections, wherein each of the multiple sections corresponds to a respective section type of multiple section types;
segment items in a first section of the multiple sections into multiple fragments, wherein the first section corresponds to a first section type of the multiple section types;
determine a section type of each of the multiple fragments in the first section;
determine whether the multiple fragments include fragments that correspond to different section types and that are interspersed among each other in even proportions; and
based on the multiple fragments in the first section including fragments that correspond to different section types and that are interspersed among each other in even proportions:
determine that the fragments that correspond to different section types and that are interspersed among each other in even proportions do not belong in the first section;
generate a new section corresponding to a section type that corresponds to a section type that is different than the multiple section types; and
re-locate the fragments that correspond to different section types and that are interspersed among each other in even proportions to the new section.

12. The computer program product of claim 11, wherein the program instructions are executable by the processor to cause the processor to determine that the multiple fragments include fragments that correspond to different section types and that are interspersed among each other in even proportions when the fragments that correspond to different section types and that are interspersed among each other in even proportions are in an alternating fashion.

* * * * *